United States Patent [19]

Wennerberg

[11] Patent Number: 5,066,865
[45] Date of Patent: Nov. 19, 1991

[54] SINGLE SIDED REFLECTANCE SENSOR FOR MEASURING SELECT PHYSICAL PROPERTIES OF A MATERIAL USING ONE OR MORE WAVELENGTHS OF RADIATION

[75] Inventor: Gunnar Wennerberg, Cupertino, Calif.

[73] Assignee: Measurex Corporation, Cupertino, Calif.

[21] Appl. No.: 401,942

[22] Filed: Sep. 1, 1989

[51] Int. Cl.$^5$ .............................................. G01N 21/88
[52] U.S. Cl. ..................................... 250/572; 356/446
[58] Field of Search ....................... 250/559, 571, 572; 356/430, 445, 447, 448, 446

[56] References Cited

U.S. PATENT DOCUMENTS

| | | | |
|---|---|---|---|
| 3,589,817 | 6/1971 | Sugaya | 250/572 |
| 3,667,846 | 6/1972 | Nater et al. | 356/376 |
| 3,804,521 | 4/1974 | Sprague | 356/446 |
| 4,004,152 | 1/1977 | Obser et al. | 250/572 |
| 4,004,153 | 1/1977 | Obser et al. | 250/572 |
| 4,072,426 | 2/1978 | Horn | 356/446 |
| 4,223,346 | 9/1980 | Neiheisel et al. | 250/572 |
| 4,226,538 | 10/1980 | Van Beeck | 250/572 |
| 4,285,597 | 8/1981 | Lamprecht et al. | 356/446 |
| 4,341,473 | 7/1982 | Mast | 356/446 |
| 4,527,898 | 7/1985 | Stapleton | 356/446 |
| 4,746,805 | 5/1988 | Stapleton | 356/446 |
| 4,795,911 | 1/1989 | Kohno et al. | 250/572 |

Primary Examiner—David C. Nelms
Assistant Examiner—S. B. Allen
Attorney, Agent, or Firm—Spensley Horn Jubas & Lubitz

[57] ABSTRACT

A single sided reflectance sensor having an optical arrangement which permits accurate measurements of select physical properties of a moving sheet. The sensor comprises a protective enclosure, positioned adjacent to a sheet surface, containing an electromagnetic radiation source disposed to project an incident beam onto the sheet surface, a reflectance sensing means for sensing the intensity of the reflected portion of the incident beam, and a planar convex lens, located between the source and the sheet. The shape and orientation of the lens source and the sheet. The shape and cross-direction and/or render the sensor substantially insensitive to sheet flutter.

18 Claims, 4 Drawing Sheets

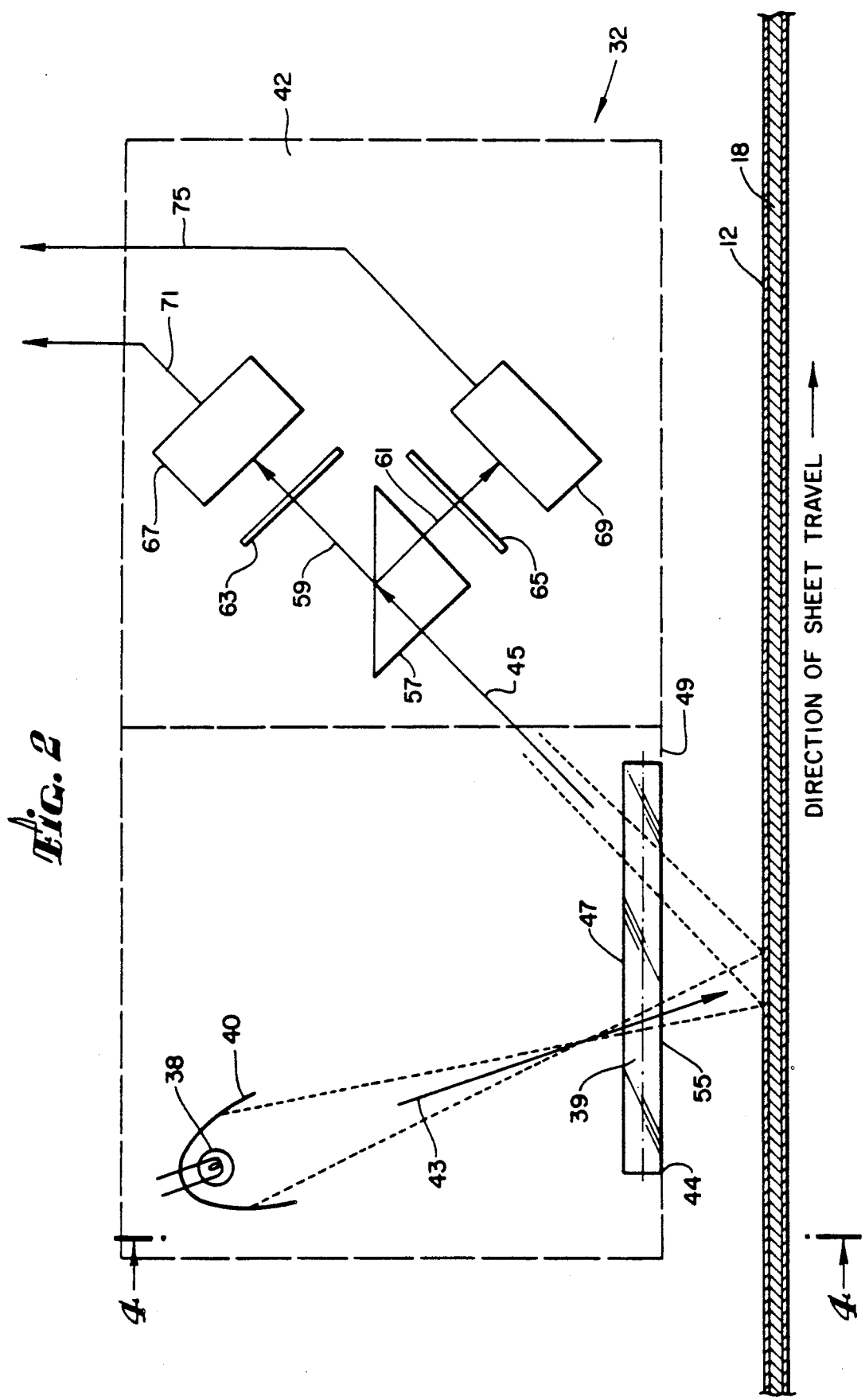

DIRECTION OF SHEET TRAVEL
IS TOWARD THE READER

DIRECTION OF SHEET TRAVEL →

SINGLE SIDED REFLECTANCE SENSOR FOR MEASURING SELECT PHYSICAL PROPERTIES OF A MATERIAL USING ONE OR MORE WAVELENGTHS OF RADIATION

BACKGROUND OF THE INVENTION

The present invention relates to a device for measuring select physical properties of a moving sheet, and more particularly, to a single sided reflectance sensor which has an optical arrangement which permits accurate measurements of those properties across the width of the sheet, including near the edges of the sheet, and is substantially insensitive to sheet flutter.

One of the physical properties used in determining the quality of paper is the surface luster or gloss of paper. Various grades of paper having different surface gloss are produced to suit various applications. Another physical property is the amount of coating applied to a sheet of paper. Still another property is the moisture content of paper. During paper production, it is desirable to periodically or continuously measure one or more of these types of physical properties to ensure that the paper has the desired qualities.

Typically, such physical properties of paper are measured and controlled during paper production before the finished paper, which is manufactured in a continuous sheet, is packaged in the form of rolls. The rolls of paper, which are typically 25 feet or more in width, are then shipped to paper product manufacturers who may further process the paper in accordance with the intended use.

Certain devices for determining these physical properties include optical systems which direct a beam of electromagnetic radiation (e.g., visible light, ultraviolet light and/or infrared light) at a paper sheet and then measure the intensity of a beam at certain wavelengths of the electromagnetic spectrum reflected from the paper surface. Typically, the value of a select physical property of the paper is determined by comparing the intensity of one or more wavelengths of the reflected beam with the intensity of the same one or more wavelengths in the incident beam and/or the beam reflected from a standardization member having a known physical property. For example, in the case of measuring the gloss of a paper sheet, the intensity of the beam reflected from the paper is compared to the intensity of the beam reflected from a glass standardization tile having a polished surface with a known gloss. More specifically, in measuring the reflectance of the paper, the electromagnetic radiation beam is projected onto the paper surface, and a reflectance sensing means, such as a photocell or photoresistor, located on the same side of the paper and which is responsive to the intensity of certain electromagnetic radiation, measures the intensity of the electromagnetic radiation reflected from the paper surface. The sensor measures the reflectance of the standardization member in the same manner by substituting the standardization member for the paper surface. The reflectance of the paper surface is then referenced to the reflectance of the standardization member, thereby providing a measure of the gloss of the paper.

In practice, the reflectance measurement of the paper is typically made at approximately six inch intervals or "slices" as the sensor scans back and forth across the width of the paper. This spacing between measurements is usually sufficient to ensure uniformity of the select physical property in the cross-direction of relatively large paper rolls. For this purpose the electromagnetic radiation source may project a circular shaped beam of approximately 1.5-2.0 inches in diameter onto the paper surface.

Single sided reflectance sensors must meet certain conditions in order to obtain accurate measurements. The first condition is that the entire incident beam must be projected onto the paper surface; otherwise, the intensity of the reflected beam will not accurately indicate the value of the select physical property. For example, if any portion of the incident beam is projected beyond the edge of the paper, the detected intensity of the reflected beam will be reduced without any actual change in the magnitude of the select physical property. If the precise location of the paper edge is unknown, the source of the change in intensity will be unknown. Thus, measurements near the edge of the paper become inaccurate and unreliable.

This condition limits the ability to accurately measure the select physical properties near the edge of the paper, particularly where there is sheet movement in the cross-direction. At best, the center of a circular shaped beam cannot be located closer than half the diameter from the paper edge. Where the sensor is being used to measure and control the amount of coating applied to paper, for example, the unmeasurable portion of the coated paper near the edge must be trimmed away to avoid reel building problems.

The second condition is that the entire beam must be projected within the slice width to be controlled; otherwise, the intensity of the reflected radiation is not representative of the select physical property of the slice width. Thus, "tighter" cross-directional control, that is smaller than the cross-directional width of a standard beam, is not obtainable through use of a standard single sided reflectance sensor. This greatly limits the utility of standard single sided reflectance sensors in applications for plastic films and smaller photographic paper rolls, which are typically 2-5 feet in width, where tighter cross-directional control is either desirable or necessary.

Certain single sided reflectance sensors also require that, for accurate measurements, the paper remain a fixed distance from the sensor. The distance from the sensor to the plane of the sheet is called the "passline". Thus, any movement by the paper perpendicular to the passline must be minimized, that is, the paper must remain steady and not flutter. The problem of sheet flutter arises during paper manufacturing when the select physical property is monitored at a location where the paper is to some extent unsupported. Typically, the single sided reflectance sensor is housed in a protective enclosure located on one side of the moving paper. The rapidly moving paper creates a rapidly moving flow of air immediately adjacent and parallel to the surface of the sheet. Upon passing by the enclosure, the airflow is distorted generating uneven air pressure on one side of the sheet, thereby producing sheet flutter. Since the intensity of the detected portion of the reflected beam varies in some manner as the distance between the sheet and the sensor changes, sheet flutter produces inaccurate measurements in single sided reflectance sensors. Minimizing sheet flutter has therefore been required to maintain an acceptable degree of accuracy in measuring select physical properties of paper.

SUMMARY OF THE INVENTION

The present invention includes an apparatus which can determine select physical properties of a sheet using measurements of radiation reflected from the sheet at least at one wavelength region of the electromagnetic spectrum. The apparatus is primarily, but not exclusively, intended for on-line measurements of the select physical properties of a moving paper sheet using various wavelengths of electromagnetic radiation. For example, moisture sensors, gloss sensors, and sensors for measuring the amount of coating material on a paper sheet, using various wavelengths of electromagnetic radiation, are well known in the papermaking industry. For the sake of simplicity, the present invention will be described in the papermaking context. However, it is understood that the invention is applicable to other situations where radiation from various regions of the electromagnetic spectrum may be utilized and the sheet material is something other than paper, such as a plastic film.

In papermaking, the sensor of the present invention may be scanned back and forth in the cross-direction of a moving sheet, to thereby provide a measurement of a select physical property at various positions along the length and the width of the sheet.

The present invention is directed toward a class of sensors called single sided reflectance sensors. These devices include a radiation source (for example, a source of visible or infrared light) and a reflectance sensing means which are positioned on the same side of the sheet within a protective enclosure. The enclosure includes an aperture. A convex lens (such as a planar-convex lens having a flat side and an opposite convex side) is disposed adjacent to the aperture for transmitting a focused beam upon the surface of the sheet, and for transmitting the beam reflected from the surface of the sheet to the reflectance sensing means. The reflectance sensing means may comprise one or more photodetectors which measure the intensity of the reflected beam at a wavelength region which is particularly sensitive to the select physical property of the paper.

In operation, the radiation source directs a beam of radiation toward a sheet surface. Before the beam reaches the sheet, it passes through the lens, which is located between the radiation source and the sheet surface. The convex surface of the lens causes the beam to converge so that the beam projected upon the sheet is smaller than the beam impinging upon the lens. The focused beam then passes through the aperture located in the wall of the enclosure.

The reflected portion of the beam is then directed to a photodetector, or if necessary, to an optical beam splitter which divides the beam into two or more separate beams. In either case, each beam is directed to a photodetector of the reflectance sensing means, amplified, digitized and sent to a computer for calculation of the select physical property. The computer compares this measurement with a desired value for the select physical property. The computer then generates a control signal that can be used to adjust process control equipment to maintain the desired value of the select physical property at each cross-directional position.

In one embodiment, the convex surface of the planar convex lens is cylindrical shaped. The lens is oriented so the lengthwise axis of the lens is parallel to the direction of sheet travel, while the ends of the lens are parallel to the cross-direction of the sheet. This orientation of the lens further confines the beam in the cross-direction, thereby permitting tighter cross-directional measurements. Thus, this particular embodiment is well suited for measurements near the edge of the sheet.

In another embodiment, the elongated planar-convex lens is tilted so that the lengthwise axis is no longer parallel to the direction of sheet travel. The lengthwise axis of the lens and the plane of the sheet may form a "tilt angle" of anywhere between ±25 degrees. As indicated by the plus and minus sign which prefix the tilt angle, the lens may be tilted either way, but it is preferred to tilt the lens so that the leading edge of the lens is further from the sheet surface than the trailing edge.

In either embodiment, the planar-convex lens is disposed adjacent to a slot shaped aperture in the enclosure wall. The slotted aperture is oriented so that the length of the slot is parallel to the direction of sheet travel, while the aperture width is parallel to the cross-direction of the sheet. It has been found that placing the lens above the aperture, with the planar surface facing toward the sheet, results in more favorable passline tolerance. The F number, that is, the focal length of the lens to aperture width ratio, is selected to blur the beam image projected onto the sheet surface, which is believed to reduce passline sensitivity.

In many situations, it is useful to use an elongated lens disposed lengthwise along the direction of sheet movement. In this way, the cross-directional width of the beam can be narrow, so that the sensor can detect narrow "streaks" running in the direction of sheet travel, while still allowing enough incident light to impinge on the sheet so as to have a sufficiently intense reflected beam to provide useful reflectance measurements. Nevertheless, in still another embodiment, the planar-convex lens is circular shaped, rather than elongated. The convex surface of the lens is spherically shaped which blurs the beam image projected onto the sheet surface and thus reduces passline sensitivity. This particular embodiment is useful for measurements of a sheet not having significant streak resolution problems.

In any of the above embodiments, the lens can be oriented so that the convex surface faces either away or towards the radiation source. However, it is preferable to orient the lens so that the convex surface faces toward the radiation source and the planar surface faces toward the sheet surface for the purpose of mounting the lens within the enclosure, and more importantly, to reduce passline sensitivity.

BRIEF DESCRIPTION OF THE DRAWINGS

FIG. 2 is a simplified schematic cross-sectional view of the sensor of FIG. 1, which illustrates the location of the optical components in a protective enclosure.

DESCRIPTION OF THE PREFERRED EMBODIMENTS

The following description is of the best presently contemplated mode of carrying out the invention. In the accompanying drawings, like numerals designate like parts in the several figures. This description is made for the purpose of illustrating the general principles of the invention and should not be taken in a limiting sense. The scope of the invention is best determined by reference to the accompanying claims.

Figure 1:
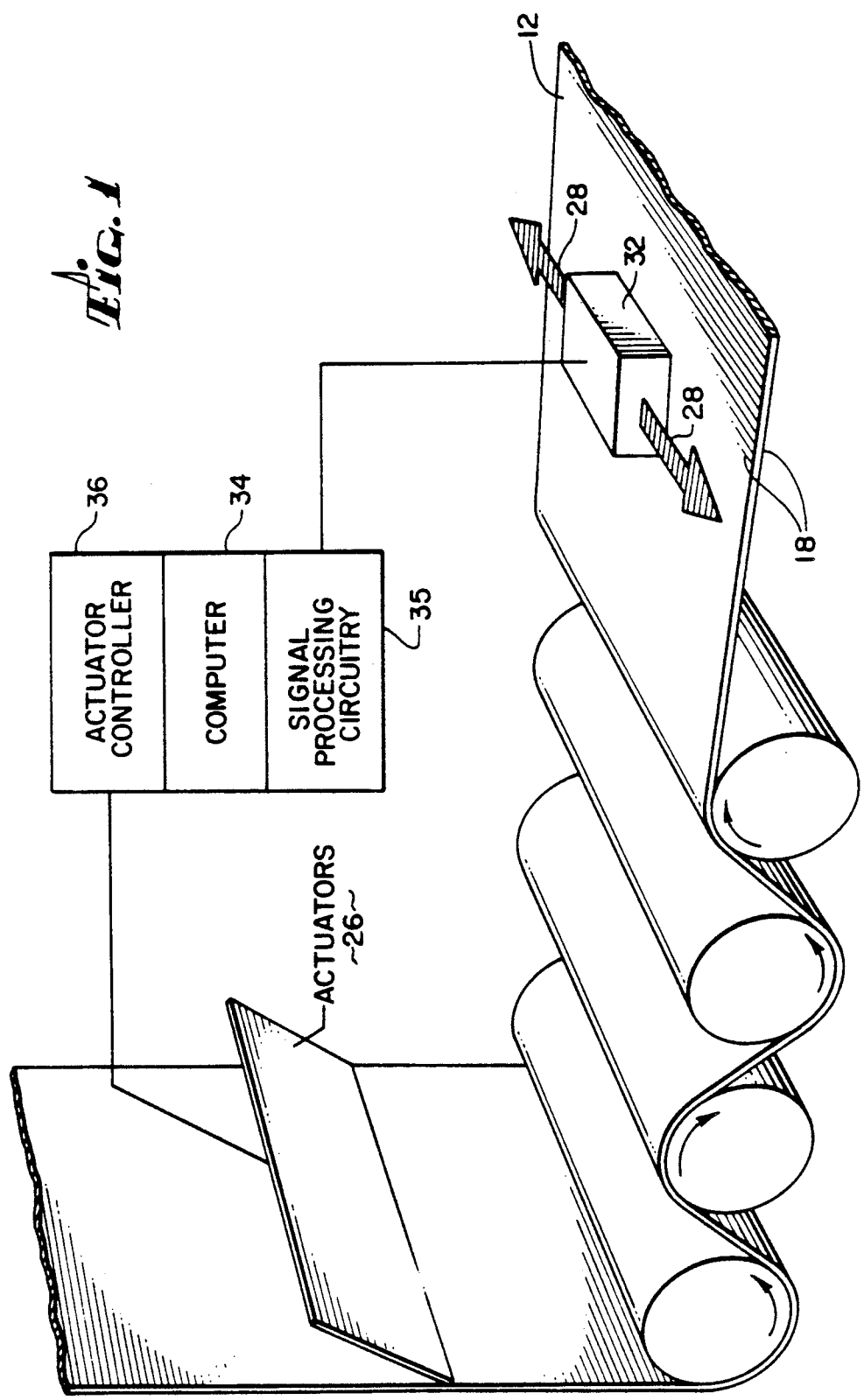
FIG. 1 is a simplified perspective view of a single sided reflectance sensor located adjacent to a sheet surface and a sheet processing control system for selectively controlling one or more actuators to control a physical property of the sheet.

A single sided reflectance sensor 32 of the present invention is shown in FIG. 1. The sensor 32 of the present invention may be used to measure the physical properties of many different types of sheet material. However, for convenience, the present invention will be described hereafter with reference to measuring physical properties of a sheet of paper 18 using infrared radiation. The body of the sensor 32 is made up of a protective enclosure containing optical components of a device which will be described later. The sensor 32 is placed adjacent to a sheet surface 12 of the paper 18 whose select physical property is to be measured. The sensor 32 is driven back and forth across the width of the paper 18, in the direction of the arrows 28, in a scanning motion so that it is able to measure the amount of radiation reflected from the paper 18 at various slice positions across the width and length of the paper 18. The measurements can be taken at relatively small intervals across the width of the paper 18.

The sensor 32 sends signals corresponding to the detected intensity of the reflected beam at one or more infrared wavelengths to a computer 34, via signal processing circuitry 35. The computer 34 relates the signals to particular slice widths of the paper 18. The computer 34 then determines the select physical property of the paper at each slice by performing various calculations, which are known in the art, based on the signals. The computer 34 then compares the measured physical property for each slice to a desired value and instructs the actuator controller 36 to send control signals to a set of actuators 26 associated with process control equipment for controlling various physical properties of the sheet. The type of actuators 26 used will vary depending on the application, and are simply illustrated in schematic form as a rectangle in FIG. 1. For example, the actuators 26 may include steam or water valves, for varying the moisture of the sheet, devices for moving a coater blade relative to a paper sheet to increase or decrease the amount of coating on a sheet or thermally operated diebolts for controlling the caliper of a plastic film. A uniform value for the select physical property across the cross-direction of the paper is the typical goal.

Figure 4:
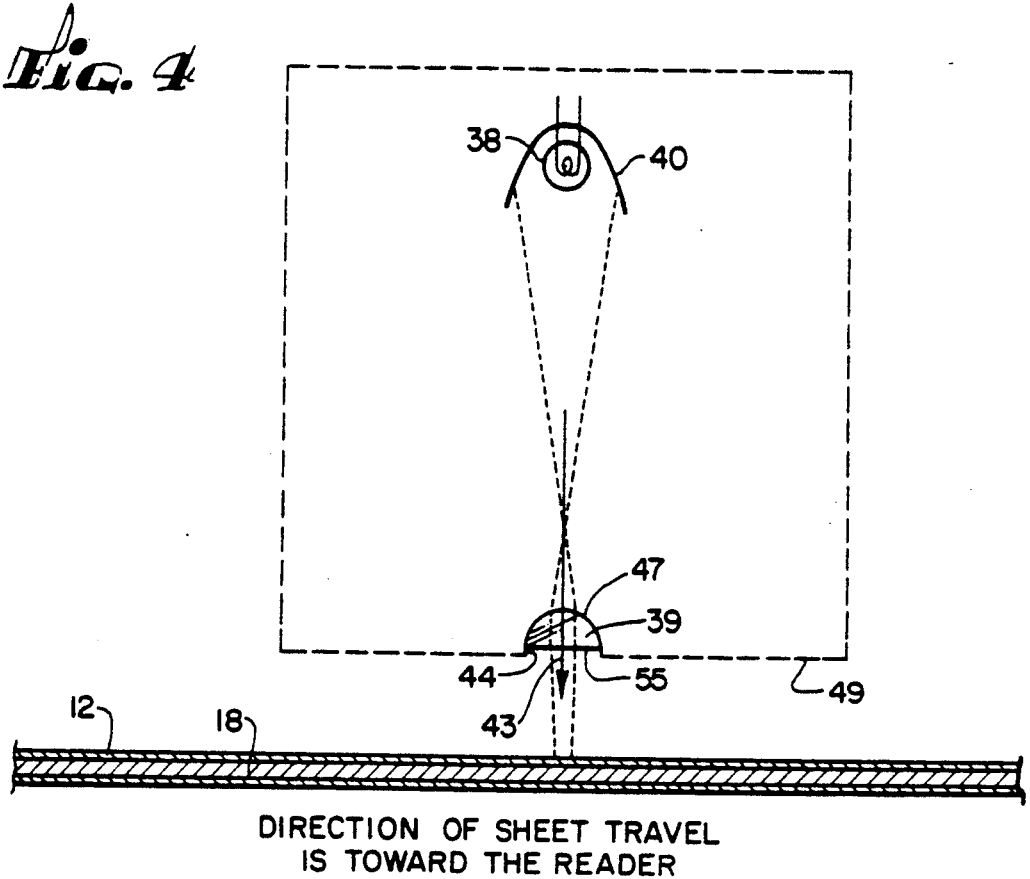
FIG. 4 is an end view taken along line 4—4 of FIG. 2 illustrating the planar-convex lens and its location with respect to certain optical components of the sensor.

The sensor 32 of FIG. 1 is illustrated in greater detail in FIG. 2. The sensor includes an incandescent lamp 38 which is used as the infrared radiation source and an eliptical reflector 40 which directs an incident beam 43 from the radiation source 38, toward the sheet surface 12 of the paper 18. Before the beam 43 reaches the sheet surface 12 it passes through a planar-convex lens 39, which is located between the radiation source 38 and the sheet surface 12. As shown in FIG. 4, the convex surface 47 of the lens 39 causes the beam 43 to converge so that the beam 43 projected onto the sheet surface 12 is smaller than the beam 43 impinging upon the lens 39. The degree of convergence is approximately proportional to the ratio of the distance between the sheet surface 12 and the lens 39 to the distance between the lens 39 and the radiation source 38. The beam 43 then passes through an aperture 44 located in the wall of enclosure, which is shown as facing toward the sheet surface 12.

As shown in FIG. 2, the reflected portion of beam 43, that is, beam 45, is directed to reflectance sensing means 42. In a typical arrangement, the reflectance sensing means 42 comprises an optical beam splitter 57, such as a half-silvered mirror, which divides the beam 45 into two separate beams 59, 61. Beams 59 and 61 are directed to bandpass filters 63, 65, which pass the desired wavelength regions to photodetectors 67, 69, respectively. At least one wavelength region is selected so that it is particularly sensitive to the select physical property of the paper 18 which one desires to measure. The second wavelength region may be used as a reference for measuring variations in intensity of the first wavelength region. In any event, the photodetectors 67, 69, then measure the intensity of each beam 59, 61, respectively, at the desired wavelength region. The output 71, 75 of each photodetector 67, 69, is then amplified, digitized and sent by signal processing circuitry 35 to a computer 34 (shown in FIG. 1) for calculation of the select physical property. As described earlier in connection with FIG. 1, the computer 34 compares the measured value of the select physical property with a desired value. The computer 34 then transmits a control signal based on the difference between the measured value and the desired value to an actuator controller 36 that is used to adjust a set of actuators 26, which activate process control equipment to achieve the desired value of the select physical property at each cross-directional position.

As shown in FIG. 2 and FIG. 4, in one embodiment, the convex surface of the lens 39 is cylindrical shaped. The lens 39 is oriented so that the lengthwise axis 48 of the lens 39 is parallel to the direction of sheet travel while the ends of the lens 39 are parallel to the cross-direction of the paper 18. This orientation of the lens 39 confines the beam 43 in the cross-direction, thereby permitting tighter cross-directional measurements. Thus, this particular embodiment is well suited for measurements near the edge of the paper 18 and for measurements where streak resolution may be a problem.

Figure 3A:
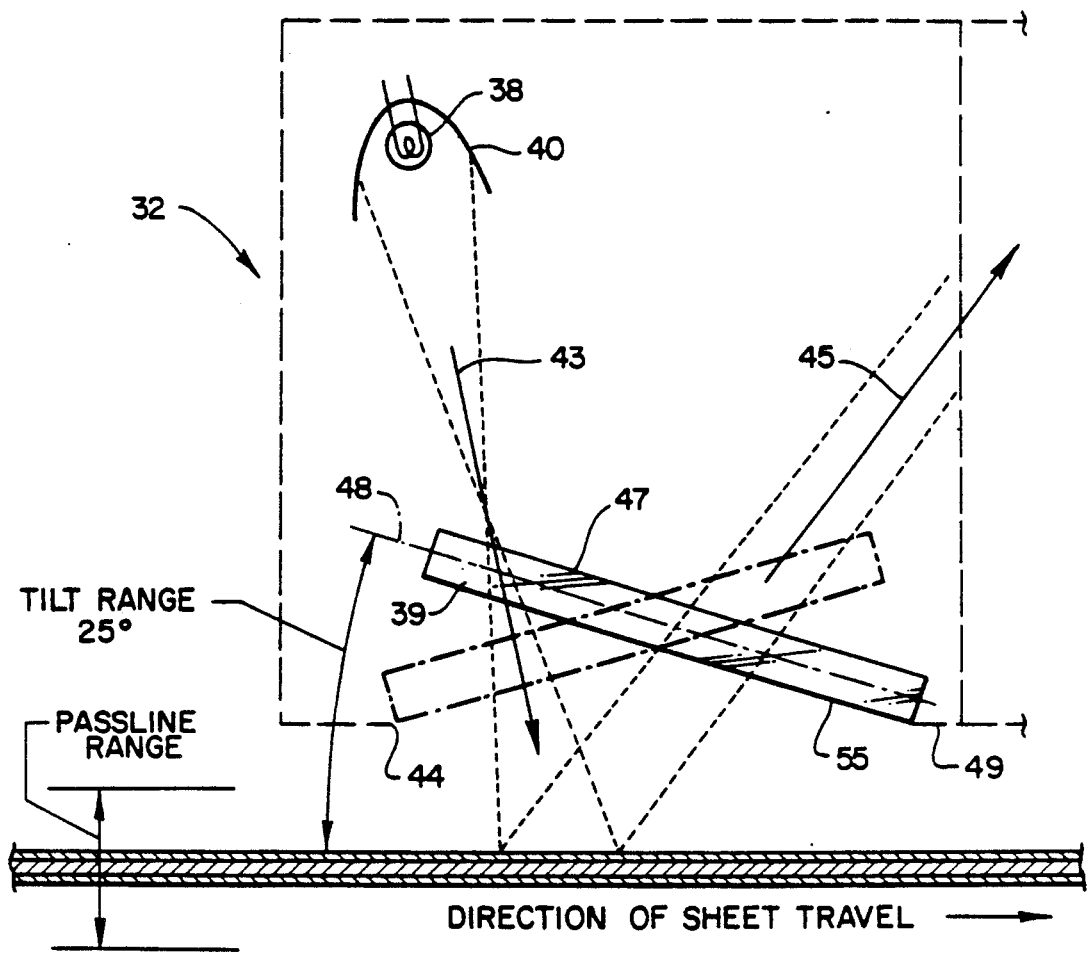
FIG. 3a is an enlarged elevation view of the planar-cylindrical convex lens, which is tilted so that the lengthwise axis is no longer parallel to the direction of sheet travel.

As shown in FIG. 3a, in another embodiment, the planar-convex lens 39 is tilted so that the lengthwise axis 48 is no longer parallel to the direction of sheet travel. The lengthwise axis 48 of the lens 39 and the direction of sheet travel may form a "tilt angle" of anywhere between ±25 degrees at the trailing edge 51 of the lens 39. As indicated by the plus and minus sign which prefix the tilt angle, the lens 39 may be tilted either way, but it is preferred to tilt the lens 39 so that the leading edge 53 of the lens 39 is further from the sheet surface 12 than the trailing edge 51. This orientation offers more safety margin against specular reflection from the lens 39 surface reaching either of the photodetectors 67, 69.

Figure 3B:
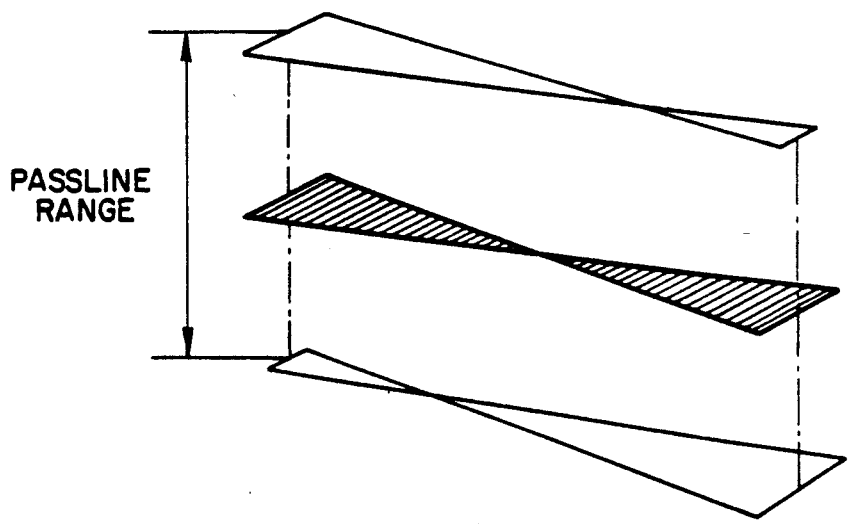
FIG. 3b illustrates the hourglass shaped pattern projected onto the sheet surface by the beam formed by the tilted lens at discrete positions within the passline range.

The tilted lens 39 reduces the passline sensitivity of the sensor 32 within a certain range measured normal to the sheet surface 12 and having its midpoint located at the optimal position of sheet travel. This range, which is referred to as the "passline range" (shown in FIG. 3a and FIG. 3b) is believed to be approximately equal to the sine function of the tilt angle multiplied by the axial length of the lens 39. Thus, increasing the tilt angle will increase the passline range where the sensor 32 is relatively passline insensitive. The tilted lens 39 is believed to reduce passline sensitivity by forming a beam 45 of relatively constant detected intensity within the passline range. As shown in FIG. 3b, the beam 43 projects an hourglass pattern onto the sheet surface 12 when the paper 18 is within the passline range so that some portion of the beam 43 will always be in focus.

As shown in FIG. 3a and FIG. 4, the planar-cylindrical convex lens 39 is disposed adjacent to a slot shaped aperture 44 in the enclosure wall 49. The slotted aperture 44 is oriented so that the length of the aperture 44 is parallel to the direction of sheet travel, while the aperture 44 width is parallel to the cross-direction of the paper 18. It has been found that placing the lens 39 above the slotted aperture 44, with the planar surface 55 facing toward the sheet surface 12, results in more favorable passline tolerance. The F number is selected to blur the beam 43 projected onto sheet surface 12, which reduces passline sensitivity. Favorable results have been obtained when the F number is anywhere between F:2 to F:8.

Figure 5:
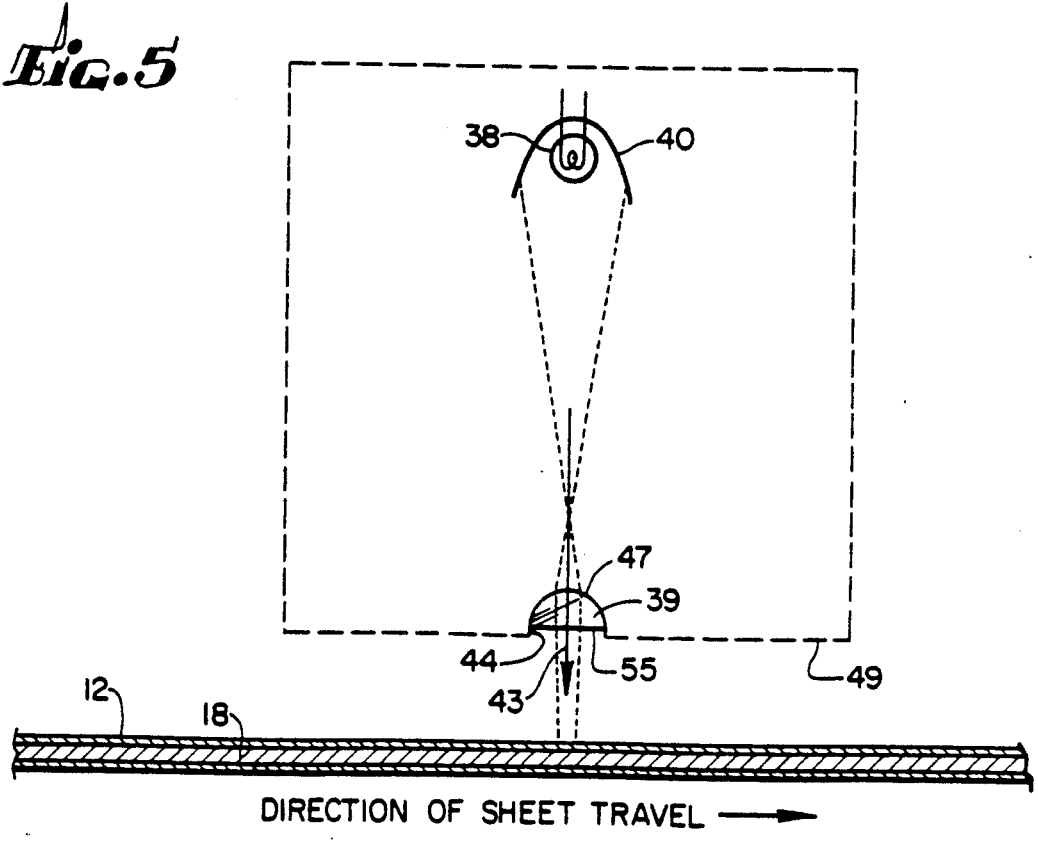
FIG. 5 is an elevation view illustrating the circular shaped planar-convex lens and its location with respect to certain optical components of the sensor.

As shown in FIG. 5, in still another embodiment, the planar-convex lens 79 is circular shaped when viewed from above. The convex surface of the lens 79 is spherically shaped which blurs the beam 43 image projected onto the sheet surface 12 to reduce passline sensitivity. This particular embodiment is useful for accurate measurements of a sheet of material not having significant streak resolution problems.

In any of the above embodiments, the lens 39 and lens 79 can be oriented so that the convex surface 47 faces either away or towards the radiation source 38. However, it is preferable to orient the lens 39 and lens 79 so that the convex surface 47 faces toward the radiation source 38 and the planar surface 55 faces toward the sheet surface 12 for the purpose of mounting the lens 39 and lens 79 within the enclosure, and more importantly, to achieve greater passline insensitivity.

Several different embodiments of the present invention has been described in detail above. Nevertheless, it is understood that one may make various modifications without departing from the spirit and scope of the invention. For example, the present invention can be utilized as described above to measure and control a wide variety of select physical properties beside the gloss, the moisture content, and the amount coating applied to paper. The property measured will depend upon the wavelengths used and the sensitivity of each wavelength to the particular sheet property. Moreover, the present invention is not limited to use with paper, nor to use with infrared radiation The present invention is also applicable to other sheet materials as well as other regions of the electromagnetic spectrum. Thus, the scope of the invention is not limited to the embodiments described in detail above.

I claim:

1. A sensor, substantially insensitive to sheet flutter, for measuring a select physical property of a traveling sheet having a machine-direction and a cross-direction, and first and second major surfaces, comprising:
   an electromagnetic radiation source disposed for projecting an incident beam onto the first surface of the sheet;
   an elongated convex lens located in the optical path between the electromagnetic radiation source and the first surface of the sheet, for projecting the beam onto the first surface of the sheet, the lens being disposed with respect to the sheet so that the lengthwise axis of the lens and the machine-direction of the sheet form an angle of anywhere between ±25 degrees at the trailing edge of the lens and so that the beam projected onto the first surface of the sheet is smaller in the cross-section than in the machine direction; and
   reflectance sensing means for sensing the intensity of the portion of the beam reflected from the first surface of the sheet.

2. The sensor of claim 1, wherein the convex surface of the lens is cylindrical shaped.

3. The sensor of claim 1, wherein the reflectance sensing means includes a plurality of photodetectors, each photodetector measuring the intensity of a separate wavelength region of the beam reflected from the first surface of the sheet.

4. The sensor of claim 1, wherein the lens is a planar-convex lens having a convex surface facing toward the electromagnetic radiation source.

5. The sensor of claim 4, further comprising an enclosure housing the electromagnetic radiation source and the reflectance sensing means, the enclosure having a wall, the wall including an aperture, the lens disposed adjacent to the aperture for transmitting the projected beam onto the first surface of the sheet.

6. The sensor of claim 5, wherein the aperture is slot shaped and wherein the focal length of the lens to the aperture width form a ratio of anywhere between 0.5:1 to 16:1.

7. The sensor of claim 1, wherein the lens is a planar-convex lens having a convex surface facing away from the electromagnetic radiation source.

8. The sensor of claim 7, further comprising an enclosure housing the electromagnetic radiation source and the reflectance sensing means, the enclosure having a wall, the wall including an aperture, the lens disposed adjacent to the aperture for transmitting the projected beam onto the first surface of the sheet.

9. The sensor of claim 8, wherein the aperture is slot shaped and wherein the focal length of the lens to the aperture width form a ratio of anywhere between 0.5:1 to 16:1.

10. A sensor, substantially insensitive to sheet flutter, for measuring select physical properties of a traveling sheet having first and second major surfaces, including near the edges thereof, comprising:
    an electromagnetic radiation source disposed for projecting an incident beam onto the first surface of the sheet;
    a planar convex lens located in the optical path between the electromagnetic radiation source and the first surface of the sheet, wherein the lens is oriented with respect to the first surface of the sheet so that the lengthwise axis of the lens and the machine-direction of the sheet form an angle of anywhere between ±25 degrees at the trailing edge of the lens and so wherein the convex surface is cylindrical shaped for projecting the beam onto the first surface of the sheet; and
    reflectance sensing means for sensing the intensity of the portion of the beam reflected from the first surface of the sheet.

11. The sensor of claim 10, wherein the reflectance sensing means includes a plurality of photodetectors, each photodetector measuring the intensity of a separate wavelength region of the beam reflected from the first surface of the sheet.

12. The sensor of claim 10, wherein the convex surface of the lens is facing toward the electromagnetic radiation source.

13. The sensor of claim 12, further comprising an enclosure housing the electromagnetic radiation source and the reflectance sensing means, the enclosure having a wall, the wall including an aperture, the lens disposed adjacent to the aperture for projecting the projected beam onto the first surface of the sheet.

14. The sensor of claim 13, wherein the focal length of the lens to aperture form a ratio of anywhere between 0.5:1 to 16:1.

15. The sensor of claim 14, wherein the convex surface of the lens is facing away from the electromagnetic radiation source.

16. The sensor of claim 15, further comprising an enclosure housing the electromagnetic radiation source and the reflectance sensing means, the enclosure having a wall, the wall including an aperture, the lens disposed adjacent to the aperture for transmitting the projected beam onto the first surface of the sheet.

17. The sensor of claim 12, wherein the focal length of the lens to aperture form a ratio of anywhere between 0.5:1 to 16:1.

18. A sensor for measuring select physical properties of a sheet having first and second major surfaces, the sensor being substantially insensitive to sheet movement in a direction normal to the first surface of the sheet, comprising:

an electromagnetic radiation source disposed for projecting an incident beam onto the first surface of the sheet;

reflectance sensing means for sensing the intensity of a portion of the beam reflected from the first surface of the sheet; and means, located in the optical path between the source and the first surface of the sheet, for redirecting the beam so that the intensity of the beam reflected from the first surface of the sheet remains substantially the same in magnitude when the sheet moves in a direction normal to the plane of the sheet.

* * * * *